US007407752B2

(12) United States Patent
Kriesel et al.

(10) Patent No.: US 7,407,752 B2
(45) Date of Patent: Aug. 5, 2008

(54) OLIGONUCLEOTIDE COMPLEXES FOR USE AS ANTI-VIRAL THERAPEUTICS

(75) Inventors: John D. Kriesel, Holladay, UT (US); Brandt B. Jones, Bountiful, UT (US); Charles B. Grissom, Salt Lake City, UT (US); Geoff Herpin, Salt Lake City, UT (US); Peter M. Glazer, Guilford, CT (US)

(73) Assignees: University of Utah Research Foundation, Salt Lake City, UT (US); Yale University, New Haven, CT (US)

( * ) Notice: Subject to any disclaimer, the term of this patent is extended or adjusted under 35 U.S.C. 154(b) by 0 days.

(21) Appl. No.: 10/830,287

(22) Filed: Apr. 21, 2004

(65) Prior Publication Data

US 2005/0038238 A1 Feb. 17, 2005

Related U.S. Application Data

(60) Provisional application No. 60/464,270, filed on Apr. 21, 2003.

(51) Int. Cl.
*C12Q 1/68* (2006.01)
*A61K 39/245* (2006.01)
(52) U.S. Cl. ........................................ 435/6; 424/231.1
(58) Field of Classification Search .................. 435/5, 435/69.1; 424/232.1
See application file for complete search history.

(56) References Cited

OTHER PUBLICATIONS

Jendis et al. AIDS Research and Human Retroviruses, 1998, 14(11):999-1005.*
Vasquez, Karen M.; Narayanan, Latha; Glazer Peter M. Specific Mutations Induced by Triplex-Forming Oligonucleotides in Mice, Science, Oct. 20, 2000, 530-533, v. 290.
Chan, Phillip P.; Glazer, Peter M. Triplex DNA: fundamentals, advances, and potential applications for gene therapy, J. Mol. Med., 1997, 267-282, v.75.
Ebbinghaus, S.W. et al. Inhibition of transcription elongation in the HER-2/neu coding sequence by tiplex-directed covalent modification . . . , Biochem, 1999, 619-628, v. 38.
Majumdar, A. et al. Targeted gene knockout mediated by triple helix forming oligonucleotides, Nature Genetics, Oct. 1998, 212-214, v. 20.
Barre, F.-X. et al. Covalent crosslinks introduced via a triple helix-forming oligonucleotide coupled to psoralen . . . , Nucleic Acids Research, 1999, 743-749, v. 27(3).
Block, Timothy M.; Hill, James M. The latency associated transcripts (LAT) of herpes simplex virus: still no end in sight, J. NeuroVirology, 1997, 313-321, v. 3.
McShan, W. M. et al. Inhibition of Transcription of HIV-1 in Infected Human Cells by Oligodeoxynucleotides . . . , J. Biological Chem., Mar. 15, 1992, 5712-5721, v. 267(8).
Helene, C. et al. Control of Gene Expression by Triple Helix-Forming Oligonucleotides: The Antigene Strategy, Annals New York Academy of Sciences, Oct. 28, 1992, 27-36, v. 660.
Oh, D.H. et al. Binding and Photoreactivity of Psoralen Linked to Triple Helix-Forming Oligonucleotides, Photochemistry and Photobiology, 2000, 298-307, v. 72(3).
Cooney, M. et al. Site-Specific Oligonucleotide Binding Represses Transcription of the Human c-myc Gene in Vitro, Science, Jul. 22, 1988, 456-459, v. 241.
Felber, T.D. et al. Photodynamic Inactivation of Herpes Simplex, JAMA, Jan. 15, 1973, 289-292, v. 223(3).
Aurelian, L. et al. Herpes Simplex Virus Type 2 Growth and Latency Reactivation by Cocultivation . . . , Antisense & Nucleic Acid Drug Development, 2000, 77-85, v. 10.
Yoon, K. et al. Targeted gene correction of episomal DNA in mammalian cells mediated by a chimeric . . . , Proc. Natl. Acad. Sci., Mar. 1996, 2071-2076, v. 93.
Jing, N. et al. Structure-Activity of Tetrad-forming Oligonucleotides as a Potent Anti-HIV Therapeutic Drug. J. Biological Chem., Dec. 25, 1998, 34992-34999, v. 273(52).
Shogan, B. et al. Virucidal Activity of a GT-Rich Oligonucleotide Against HSV Mediated by GB. 29th International Herpesvirus Workshop, Jul. 25-30, 2004. abstract.
Morales-Rojas, H. and Kool, E.T. A Porphyrin C-Nucleoside Incorporated into DNA. Organic Letters, 2002, 4377-4380, v. 4(25).

* cited by examiner

*Primary Examiner*—Stacy B Chen
(74) *Attorney, Agent, or Firm*—The McCallum Law Firm, P.C.; Jennifer M. McCallum, Esq.

(57) ABSTRACT

The methods disclosed herein are of use for the treatment of a wide variety of diseases. In particular, the methods provide for the targeting of a transcription altering agent to a specific target site of a viral genome in order to inactivate the virus. In addition, the methods provide for a triplex-forming oligonucleotide capable of interacting with a target site in a viral genome in order to alter transcription. The methods of the present invention may be used against viral pathogens or agents of bioterrorism.

3 Claims, No Drawings

OLIGONUCLEOTIDE COMPLEXES FOR USE AS ANTI-VIRAL THERAPEUTICS

REFERENCE TO RELATED APPLICATIONS

This is a United States Utility Patent Application claiming priority to U.S. Provisional Application Ser. No. 60/464,270 filed Apr. 21, 2003 and hereby incorporated by reference in its entirety.

STATEMENT REGARDING FEDERALLY SPONSORED RESEARCH

A portion of this work was funded by NIH/NEI Grant No. 1R29EY11732 and the US Government may have certain rights in this invention.

FIELD OF THE INVENTION

The present invention relates to compositions and methods useful in the treatment or prevention of a viral infection.

BACKGROUND

Latent viruses pose a serious health problem because they continually re-infect their host. It is believed they do this via transcription of latency-associated transcripts (LATs), which produce RNAs that are not translated into proteins to lessen the chance of detection and/or elimination by the host immune system.

In humans, they include all of the herpes viruses, such as HSV-1, HSV-2, VZV, CMV, EBV, HHV-6, HHV-7 and HHV-8, for example. Other latent viruses include the human polyoma viruses (JC and BK viruses), adenoviruses and Human Immunodeficiency Virus (HIV). These viruses are associated with a number of clinical conditions including recurrent herpes labialis, such as cold sores or HSV-1; genital herpes, such as HSV-2; various types of cancer, such as EBV or HHV-8; multi-organ or systemic infections, such as CMV; progressive multifocal leukoencephalopathy, such as the JC virus and AIDS, for example.

One such latent virus is HSV-1, which causes herpes keratitis. HSV-1 infection of the corneal surface is perhaps the most serious of all HSV-induced diseases. This ophthalmologic disease is difficult to treat, recurs unexpectedly, and often leads to corneal scarring and blindness. There are approximately 20,000 new cases of herpes keratitis annually in the U.S. and 28,000 recurrent cases, leading to 6000 corneal transplants. It is a recurrent disease where HSV-1 reactivation in the ganglion leads to repeated infections in the cornea with subsequent scarring and opacity. Daily prophylactic acyclovir—an effective strategy for prevention of genital HSV-2 recurrences—is much less effective against HSV-1 ocular recurrences. A quantum leap in the ability to prevent ocular HSV-1 recurrences is greatly needed for these patients.

Another example of a latent virus is human papillomavirus (HPV) that is one of the most common sexually transmitted diseases in the world. Approximately 5.5 million new cases of sexually transmitted HPV are reported each year and it is estimated that at least 20 million Americans are already infected. More than 100 different types of HPV have been identified and approximately 30 of these are spread by sexual contact. Many types of HPV can cause cervical or genital cancer.

HPV can cause genital warts that often disappear without treatment but they almost always reoccur. Several treatment options exist but they are uncomfortable, expensive and a temporary measure. Creams, such as Imiquimod, podophyllin anti-mitotic solutions, podofilox solutions, fluorouracil cream or trichloroacetic acid may be applied to the lesions themselves. Other treatment options include cryosurgery, electrocautery, laser treatment or surgery. Additionally, the antiviral drug alpha interferon may be injected directly into genital warts but this therapy is extremely expensive and does not offer a reduced re-infection rate over other treatment options.

There are currently no permanent methods of disabling a latent viral infection. Current therapies merely stop replication of a few viruses but do not affect latent viruses themselves, thus allowing for recurrent viral infection. A direct method of permanently curing latent viral infections is greatly needed.

SUMMARY OF THE INVENTION

The present invention embodies compositions and methods related to triplex oligonucleotide (known as "triplex oligo", "TFO", or "antigene") technology. These compositions and methods are useful for treating viral infections, particularly those caused by double stranded DNA viruses, or viruses which have double stranded DNA for at least a part of the viral life cycle. The methods and compositions of the present invention can be used against common viral pathogens or agents of bioterrorism. In one embodiment, the present invention provides for compositions and methods for treating diseases caused by latent viruses. These viruses include, but are not limited to all of the human herpes viruses (for example, HSV-1, HSV-2, VZV, CMV, EBV, HHV-6, HHV-7, AND HHV-8), and also other latent viruses, for example JC virus, adenovirus, and HIV. One embodiment of the present invention provides for compositions and methods for effective anti-latency therapy to prevent recurrences and halt progression of herpes keratitis or genital herpes. This novel genetic therapy could potentially prevent thousands of episodes of recurrent viral infections each year.

In another embodiment the methods and compositions of the present invention can be used to treat disease caused by double-stranded DNA viruses, including, but not limited to members of the Adenoviridae, Herpesviridae, Papillomaviridae, Polyomaviridae, and Poxviridae families. Some members of these virus families include Human adenovirus A, herpes simplex type 1, human papillomavirus type 1a, JC virus, and variola.

According to the methods of the present invention, TFO target sites are found within the genomes of all viruses. In a particular embodiment, the virus is selected from the group consisting of smallpox, vaccinia, cowpox, monkeypox, and camelpox, Human adenovirus A, herpes simplex type 1 (HSV-1), human papillomavirus type 1a, and JC virus.

According to particular embodiments of the compositions and methods of the present invention, a triplex-forming oligonucleotide can be used to deliver a therapeutic agent to a target region of a viral genome. In one embodiment, a TFO can be delivered into trigeminal neuron and trigeminal glanglion cells, specific TFO-induced transcriptional inhibition of an HSV-1 reporter gene construct can be performed, and a reproducible and specific antiviral effect can be achieved.

The compositions and methods of the present invention further provide a method of delivering a TFO complexed with a photoactivateable pro-drug capable of interacting with a target site in a viral genome upon exposure to light, which causes release of the TFO from the photoactivateable pro-drug and disruption of viral transcription. The photoactivateable pro-drug complex may be selected from the group consisting of vitamin B12 and cobalamin analogs, porphyrins and porphyrin-like molecules, psoralen and the like. In a particular embodiment, transcription is disrupted by introduction of a mutation in the viral genome.

The TFOs of the present invention may be any oligonucleotides capable of binding to a viral genome. The TFOs of the present invention may bind to polypurine- or polypyrmidine-rich sites in the viral genome. In a particular embodiment, they bind target sequences in the variola genome selected from the group consisting of SEQ ID 3 (bp 58877), (bp82884) SEQ ID 4, (bp 139456) SEQ ID 5, (bp 5403) SEQ ID 6, (bp 13137) SEQ ID 7, ((bp 26168) SEQ ID 8, (bp 53917) SEQ ID 9, (bp 125303) SEQ ID 10, (bp 137434) SEQ ID 11 and (bp 184743) SEQ ID 12. In another particular embodiment, the TFOs are SEQ ID 1(TFO-1) and SEQ ID 2 9TFO-3).

BRIEF DESCRIPTION OF THE DRAWINGS

The following drawings form part of the present specification and are included to further demonstrate certain embodiments. These embodiments may be better understood by reference to one or more of these drawings in combination with the detailed description of specific embodiments presented herein.

DETAILED DESCRIPTION OF THE INVENTION

Definitions

For the purposes of the present invention, the following terms shall have the following meanings:

For the purpose of the present invention, "target DNA sequence," "target strand" or "target strands" refers to the DNA sequence intended to be or actually bound by the TFO.

For the purposes of the present invention, ranges may be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Moreover, for the purposes of the present invention, the term "a" or "an" entity refers to one or more of that entity; for example, "a TFO" or "an photoactivateable agent" refers to one or more of those compounds or at least one compound. As such, the terms "a" or "an", "one or more" and "at least one" can be used interchangeably herein. It is also to be noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated or biologically pure bioactive agent is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

Reference will now be made in detail to certain embodiments of the invention, examples of which are illustrated in the accompanying Detailed Description and Examples section.

Triplex Oligonucleotide Binding to the Viral Genome

Triplex formation occurs when a DNA or RNA oligonucleotide binds to a homopurine region of double-stranded DNA. These triplex-forming oligonucleotides (TFO's or triplex oligonucleotides) bind specifically in the major groove of their target DNA sequences, forming Hoogsteen or reverse Hoogsteen hydrogen bonds with bases in the purine-rich strand of the target DNA. Two different orientations may be suitable for triplex formation:

(1) Purine motif: polypurine (AG) triplex oligonucleotides running anti-parallel (5'-3'/3'-5') to its corresponding target polypurine DNA strand or (2) Pyrimidine motif: polypyrimidine (CT or CU) triplex oligonucleotides running parallel (5'-3'/5'-3') to its corresponding target polypurine DNA strand.

The purine (AG) motif exhibits largely pH-independent binding so these TFOs may be superior for triplex formation under physiologic conditions. Mismatches (C's or T's within the target polypurine AG runs) destabilize the triplex complexes; polypurine runs of at least 11 bp with no mismatches are considered to be the most suitable targets. The HSV-1, smallpox (variola), cowpox, monkeypox, camelpox, vaccinia, human adenovirus A (Adenoviridae), human papillomavirus type 1a (Papillomaviridae), and JC virus (Polyomaviridae) genome sequences, for example, contain many such long polypurine runs.

Identification of TFO Target Sites within Viral Genomes

The expected frequency of long purine/pyrimidine runs (poly-AG/poly-CT) is approximately $(1/2)^n$, where n=the number of nucleotides in the run. For instance, a poly-AG run 20 bp long has an expected frequency of $(1/2)^{20}=1/1,048,576$. The HSV genome is only 152,000 bp in length, so few if any long purine/pyrimidine runs are expected to occur by chance alone. Similar reasoning can be applied to the smallpox (185,578 bp) and vaccinia (191,737 bp) virus genomes, for example. However, sequence analysis of these viral genomes reveals many poly-AG or poly-CT runs 15 bp in length or longer. Each of these many poly-AG or poly-CT runs exceed the minimum required for stable triplex formation.

Poly-AG sequences on one viral strand are always accompanied by poly-CT runs on the other strand. Published viral genome sequences include only one strand, usually the coding strand. Since TFO's may bind to either DNA strand to induce cross-linking between the target strands, both coding and complementary strands need to be considered when searching for target sequences.

In one embodiment, the sequence analyzed is human papillomavirus (GeneBank Accession number NC 001356).

In another embodiment, the analyzed sequence is HSV. In a particular embodiment, the LAT domain sequence is bound by a TFO selected from the group consisting of SEQ ID 1 and SEQ ID 2. Target sequences including long purine/pyrimidine runs, suitable for purine motif triplex oligonucleotides, are included in the present invention. Target sequences overlapping the LAT TATA box also work well with the present invention because TFO binding may disrupt a transcription factor binding site. In a particular embodiment, a pyrimidine motif triplex oligonucleotide was chosen.

In another embodiment, the analyzed sequence is a member of the family Poxviridae. Members of this family include the poxviruses, such as variola, vaccinia, cowpox, monkeypox, and camelpox. Poxviral sequences may be obtained from the NCBI Viral Reference Genomes website. TFO target sites may be identified by searching for poly-purine/poly-pyrimidine (poly-AG/poly-CT) runs of 11 or more bp in length and by searching for the presence of the 10 specific variola sequences, for example. Using this method, a total of 229 potential TFO target sites were identified in the sequences of five poxviruses and most of these poxviral TFO target sites are located near the beginning or end of the viral genomes. The greatest number of target sites was identified within the vaccinia sequence (84) and the fewest within the variola sequence (10). Long and therefore likely unique poly-purine/pyrimidine target sites were identified in the camelpox (31 bp) and vaccinia (30 bp) sequences.

TFO target sequences of the present invention may be chosen based on their homology to the 10 known variola TFO target sites. Among these 10 variola TFO target sequences, 7 have identical sequences among one or more of other poxviruses. For instance, SEQ ID 12 is a variola TFO target site that is also found in the genomes of vaccinia (bp 188081 and 5 other sites), cowpox (bp 221999), monkeypox (bp 196238), and camelpox (bp 203680). Accordingly, the present invention encompasses the testing and development of TFO-based antipoxvirals that are expected to share activity against one or more poxviruses, such as vaccinia, cowpox, monkeypox, camelpox and smallpox. In a particular embodiment, the sequences in the variola genome are selected from the group consisting of SEQ ID 3 (bp 58877), (bp82884) SEQ ID 4, (bp 139456) SEQ ID 5, (bp 5403) SEQ ID 6, (bp 13137) SEQ ID 7, ((bp 26168) SEQ ID 8, (bp 53917) SEQ ID 9, (bp 125303) SEQ ID 10, (bp 137434) SEQ ID 11 and (bp 184743) SEQ ID 12.

Additionally, TFO target sites of the present invention may be chosen based on their uniqueness. TFO target sites of 20 or more bp in length are less likely to have homologues in the human genome than shorter sites. Selection of the longest poxviral TFO target sites and comparison with the human genome will help to ensure specificity of the proposed anti-poxviral TFOs, minimizing side-effects in humans. For instance, the longest identified camelpox TFO target site, a CT 31-mer at bp 180763 when compared with the published human genome sequence using the NCBI BLASTn application revealed no exact matches within the human genome (closest match: 24/31 nucleotides), indicating this TFO target site is unique to camelpox.

TFO target sites within the LAT of a viral genome is also contemplated by the present invention. This site may be chosen as a method of inactivating viral re-infection. In an exemplary embodiment, HSV-1 was analyzed for TFO target sites. The anti-HSV-1 TFO target sites lie within the inverted repeat region in a viral gene (LAT) that is transcribed but not translated.

In certain embodiments, TFOs may be used in combination. For example, Example 9 illustrates that triplex oligonucleotides SEQ ID 1 and 2, when utilized in combination, rather than singly, are more effective. The present invention includes administration of one, two, three or more TFOs to an individual in order to prevent a viral infection or re-infection.

Activation of Antiviral TFO's

The TFOs of the present invention do not need an activation mechanism to affect transcription of a viral genome, although an activation mechanism may be provided. As illustrated in Example 3, transcriptional inhibition of HSV-1 did not require ultraviolet light (UVA) activation.

In another embodiment, transcription of a viral genome is altered via crosslinking between the viral DNA and the TFO. This may be accomplished with UVA or through the use of modified bases (e.g. 7-deasa-2' deoxyguanosine), alkylating agents, or 5'-acridine linkage for incorporation into TFOs. Acridine-linked and alkylating TFOs are available from commercial sources (Glen Research, Sterling, Va.). Acridine has a cyclic ring structure that allows it to intercalate into the target DNA sequence and cross-link it. This compound can be linked to either the 5' or 3' end of a TFO. Acridine linkage or incorporation has the additional beneficial property of making the oligonucleotide more resistant to nucleases, potentially prolonging activity in vivo.

Additionally, TFOs may be modified by the inclusion of bromine. Such chemically modified TFOs absorb gamma radiation more readily than unmodified DNA and, therefore, are activated throughout the body by X-rays.

Method of Use as a Therapeutic

According to the present invention, highly specific triplex-forming oligonucleotides will be delivered to human or animal patients at nanomolar to micromolar concentrations to achieve an anti-viral effect. For example, triplex formation at HSV-1 LAT by SEQ ID 2 begins at a TFO concentration of 10 nM and is virtually complete at 100 nM. Many drugs are given intravenously to humans in large doses, achieving tissue levels higher than the triplex oligonucleotide levels proposed here. For instance, ampicillin/sulbactam, a commonly used intravenous antibiotic, is usually given at a dose of 2 grams four times daily. This dosing regimen achieves ampicillin steady-state tissue levels of approximately 8 μg/ml (21 μM). Acyclovir, a commonly used intravenous antiviral, reaches a similar steady-state trough concentration of 2 μg/ml (8 μM). Both of these drugs are flooded into humans, but are highly selective for their targets and therefore have little or no toxicity to the host.

The present invention provides several strategies for delivery of TFO's to a patient. These strategies include intraperitoneal and/or intravenous infusion of TFOs. In particular embodiments, the TFOs may include capped phosphodiester or phosporothioate oligonucleotides, a targeting moiety or targeting group, such as vitamin B12 or nerve growth factor (NGF), an activateable compound, such as psoralin and the like. The integrity of the delivered oligonucleotides can be determined by native gel electrophoresis of tissue, blood, or other body or cellular components or cellular extracts.

Photoactivation of anti-viral oligonucleotides is achieved by incorporation of the DNA triplex with a photoactivatable pro-drug, followed by selective delivery of tissue-penetrating red light to the trigeminal ganglion (TG) via nasal cannulation. This approach allows for accumulation of the photoactivatable TFOs in cells bearing a latent virus infection, followed by selective activation with red light. Photoactivateable compounds of the present invention may be selected from the group consisting of hematoporphyrin IX (Photofrin), chlorines, bacteriochlorins, phthalocyanines, hypocrellins and the like.

Photoactivation of the latent herpes virus may be achieved with a two-stage process: 1) Incorporation of the DNA triplex with a photoactivateable pro-drug; followed by 2) selective delivery of tissue-penetrating red light to the trigeminal ganglion via nasal cannulation. This approach allows for accumulation of the TFO in a particular location where it can be most effective. In a particular method of the present invention, the TFO is complexed with a photoactivateable compound and directed to TG cells bearing a latent herpes virus infection, followed by selective activation with red light. This treatment paradigm is based upon the success of photodynamic therapy (PDT) with the approved drug Photofrin® for the treatment of neoplastic and dysplastic lesions in the esophagus and bladder.

A photoactivateable agent, such as Photofrin or a similar heme-based chromophore, can be attached via a stable linker to single-stranded DNA that is specific for the herpes virus. Intracellular Photofrin is activated by red light (630-650 nm) in the presence of cellular oxygen to generate singlet oxygen. Subsequent radical reactions form superoxide and hydroxyl radicals that can degrade the herpes genome. This therapeutic approach is analogous to DNA-footprinting, in which hydroxyl radicals can degrade a proximal DNA strand. The dose of light delivered will be limited to produce oxygen radicals to cleave the phosphodiester backbone of the herpes DNA and not trigger an overtly cytotoxic response by oxidative overload (i.e. cellular necrosis or apoptosis).

TFOs may be conjugated to a molecule capable of directing the TFO to a particular location in a patient. For example, ganglionic neurons continuously receive Nerve Growth Factor (NGF) as it streams inward from peripheral nerve endings via the NGF receptor/transporter protein trkA. TFOs, for example, can be chemically linked to NGF in order to direct them to ganglionic neurons. The significance of this approach is that it can utilize the existing NGF transport mechanism to non-invasively shuttle TFOs from the peripheral axons (e.g. corneal surface) into the neuron cell bodies (e.g. the TG). This exemplary method can be used to direct TFOs to particular locations within a patient with a viral infection.

The TFOs of the present invention may be conjugated to cobalamin (vitamin B12). This may be useful due to enhanced neuronal uptake of a TFO linked to vitamin B12. Peripheral neuropathy is a consequence of B12 deprivation suggesting that cobalamin is taken up by and utilized by peripheral sensory neurons, including those that lie within the TG. Furthermore, virally-infected neurons may have an even greater unmet need for cobalamin to support one-carbon metabolism prior to DNA synthesis and viral replication. In support of the latter hypothesis, cancer cells are known to have an increased need for cobalamin to support one-carbon metabolism prior to DNA synthesis, and cobalamin has been used as an effective vehicle to deliver cytotoxic drugs and fluorescent diagnostic agents to tumors in vitro and in vivo.

Protection of TFOs against Nucleases.

According to the present invention, successful strategies for the protection of DNA oligonucleotides include, but are not limited to, replacing the normal phosphodiester backbone with phosporothioate. The base composition (sequence) of such sulfur-based oligonucleotides remains the same and, typically, binding to the target region is unaffected or enhanced. Phosphorothioate oligonucleotides are resistant to degradation by circulating and cellular nucleases.

EXAMPLES

It should be appreciated by those skilled in the art that the techniques disclosed in the examples which follow represent techniques discovered by the inventors to function well in the practice of the invention, and thus can be considered to constitute particular modes for its practice. However, those of skill in the art should appreciate, in light of the present disclosure, that many changes can be made in the specific embodiments disclosed herein which will still obtain a like or similar result without departing from the spirit and scope of the invention.

Example 1

Identification of Target Sites within the HSV-1 Genome

Utilizing the methods of the present invention, three triplex oligonucleotide target sequences were identified within the HSV-1 LAT domain. The first two target sites are bound by the oligonucleotides SEQ ID 1 (TFO-1) and 2 (TFO-3) and were chosen because they have long purine/pyrimidine runs, suitable for a purine motif triplex oligonucleotide. The third site overlapped the LAT TATA box and was identified as a potential transcription factor binding site.

LAT is transcribed from the HSV-1 complementary strand, resulting in an 8.3 kb primary transcript ("minor LAT") which is processed into a stable 2.1 kb lariat form ("major LAT", or "LAT intron"). The triplex oligonucleotide target region lies between the LAT promoter and the start of the major LAT. Examples presented herein include TFO's encoded by SEQ ID 1 (TFO-1) and 2 (TFO-3).

Example 2

Sequence Diversity of the HSV-1 Target Region

Sequence diversity within the HSV-1 target site region may be important to choosing targets because mismatches between the poly-AG triplex and its poly-AG/CT target will destabilize the oligonucleotide/target complex. Three clinical strains of HSV-1 were sequenced: 17 syn+, CGA-3, and Rodanus. The sequence of the (17syn+) target sequence bound by TFO-3 (SEQ ID 2) was identical to that obtained through GenBank. All 3 strains had identical sequences at and around this same target sequence. Likewise, the sequence in the TATA box region did not vary between the strains. Sequence differences were observed at 2 sites within the target sequence bound by TFO-2 (SEQ ID 1) (one single nucleotide deletion and one C-T reversion), but the perfect 20-21 bp polypurine/polypyrimidine run was preserved. This suggests there is little sequence variation in the HSV-1 target regions identified here and that many or most strains of HSV-1 will be suitable for triplex therapy directed at the HSV-1 LAT domain.

Example 3

Triplex Formation In Vitro

The target sequence bound by TFO-3 (SEQ ID 2) yielded a relatively clean duplex when end-labeled with $^{32}$P and allowed to anneal to its purine complement. One fmole (1.0 fM) [The absolute amount of target DNA was one femtomole=$1\times10^{-15}$ moles placed in solution to a concentration of 1.0 nM=1.0 nanomoles/liter] of this duplex was then incubated at 37 degrees C. with increasing concentrations of the target sequence in a binding buffer containing 10 mM Tris, pH 7.5, 1 mM spermine, 20 mM KCl, and 10% sucrose, according to a published protocol. The DNA complexes—single-strand, double-strand, and triplex—were separated in a native polyacrylamide gel. Triplex DNA complex formation was detected at a triplex:duplex ratio of 10:1. Triplex formation was virtually complete at a triplex:duplex ratio of 100:1, corresponding to a triplex oligonucleotide concentration of 100 nM, consistent with other reports in the literature and below that believed to be achievable in vivo.

Example 4

Movement of TFO-3 into Rat Neuron Cells in Culture

Trigeminal ganglia (TG) were harvested from newborn rats, disrupted, and placed into parallel NGF-supplemented (20 ng/ml) cell cultures with cytosine arabinoside (Ara-C)

added to kill non-neuronal cells. Ara-C was removed at day 7 and the cultures were allowed to mature for an additional 10 days. Counting of representative areas showed that each culture contained approximately 4000 TG neurons ranging from 20-40 μm in diameter. The target sequence bound by TFO-3 (SEQ ID 2) was labeled with $^{32}$P. Groups of 3-4 TG neuron cultures were bathed in TFO-3 (SEQ ID 2) at a concentration of 0.5 nM (+20 ng/ml NGF) for 2, 6, or 24 hours. The cultures were washed twice with cold PBS before being scraped and placed in lysis buffer for analysis. TFO-3 (SEQ ID 2) was progressively taken up into the neurons over 24 hours. The concentrations in the culture supernatants and cellular fractions were calculated using the specific activity of the original labeled oligonucleotide ($2.25 \times 10^6$ cpm/pmol), an estimated neuronal volume (14.1 μL/neuron), and the molecular weight of the oligonucleotide (7.5 kDa). These calculations revealed an average TFO-3 (SEQ ID 2) oligonucleotide ($^{32}$P) concentration of 0.44 nM in the supernatants (similar to the 0.5 nM starting concentration) and a much higher cellular concentration, 95 nM. This suggests that only about 1% of the TFO needs to be intact and transported into the nucleus to achieve the 1.0 nM concentration required for complete triplex formation in vitro.

Example 5

TFO-3 Inhibits Transcription

The luciferase-producing reporter construct pGL3 (Promega Biosciences; San Luis Obispo, Calif.) was modified to include a HSV-1 target sequence bound by SEQ ID 3 just upstream of the luciferase gene start codon (C2A). Human embryonic kidney cells (HEK-293) were transfected with pGL3 or C2A and incubated with 0, 1, or 10 μM anti-HSV-1 TFO-3 (SEQ ID 3) for 24 hours (N=5 per group). The results are given as percent of control luciferase production (reporter construct without a TFO target sequence), normalized for the protein content of each cellular extract, ±the standard error of the mean. Background luciferase production was negligible (≦1% of control values). Repeated experiments showed equivalent levels of transfection among the groups. A two-tailed Student's T-Test was used to compare each TFO group with its respective control. The anti-HSV-1 TFO significantly inhibited luciferase production when added to cells transfected with the HSV-1 Target-3 reporter construct C2A. This effect was specific; the TFO did not inhibit the parent (control) reporter construct pGL3 lacking the HSV-1 target sequence.

Example 6

Antiviral Effects of TFO's

The following Examples (Example 6-9) demonstrate a specific, reproducible, and synergistic antiviral effect of TFO 1 (SEQ ID 1) and TFO-3 (SEQ ID 2) against HSV-1. Viral titers were determined by plaque counts on Vero cell monolayers.

3000 PFU/ml of HSV-1 were incubated with 1 μM TFO-3 (SEQ ID 2) at room temperature, N=5 replications per group. Viral killing (as measured by plaque-reduction) was effected by exposing the mixture to ultraviolet-A radiation for 0, 20 and 40 minutes at room temperature. HSV-1 titers were determined by plaque assay on Vero cells. The results were confirmed by a masked observer. The results were calculated as a percent of the unirradiated (0 min.) "virus only" control titers±SEM. Statistical comparisons were made between the "virus only" and "virus+TFO-3 (SEQ ID 2)" groups at each time point using an unpaired two-tailed Student's T-Test. At time point 0, the virus only group displayed 100% of the unirradiated virus only control titer whereas the virus plus TFO-3 (SEQ ID 2) group displayed approximately 80%. At the 20 minute time point, the virus only group displayed approximately 80% of the unirridaiated virus only control titer whereas the virus plus TFO-3 (SEQ ID 2) group displayed approximately 50%. At the 40 minute time point, the virus only group displayed approximately 50% of the unirradiated virus only control group titer and the virus plus TFO-3 (SEQ ID 2) group 30%.

Example 7

Specific Antiviral Effects of TFO-3 Against HSV-1 Strain 17 Syn+

3000 PFU/ml of HSV-1 was incubated with 1 μM TFO-3 (SEQ ID 2) or a (scrambled) control oligonucleotide. Viral killing was affected by exposing the mixture to ultraviolet-A radiation for 40 min. Results are expressed as percent of the "virus only" control titers±SEM. Statistical comparisons were made to the "virus only" group using the two-tailed Student's T-Test. The virus only and virus plus control oligonucleotide groups had approximately 100% of control viral titer values, whereas the virus plus TFO-3 (SEQ ID 2) group displayed approximately 20% of control viral titer values.

Example 8

Ultraviolet A Radiation of TFO-3

HSV-1 was incubated with 1 μM TFO-3 (SEQ ID 2) with and without exposure to ultraviolet-A radiation for 40 minutes at room temperature. Results are expressed as mean viral titers±standard errors. Statistical comparisons were made using the two-tailed Student's T-Test. UVA exposure by itself caused approximately 50% viral killing (plaque-reduction), enhanced another 40% by the addition of TFO-3 (SEQ ID 2).

Example 9

Synergistic Antiviral Effects of Two TFO's Against HSV-1

HSV-1 was incubated with 1 μM of TFO-1 (SEQ ID 1) and TFO-3 (SEQ ID 2) or their scrambled control oligonucleotides. All the groups were exposed to ultraviolet-A radiation for 40 minutes at room temperature. Results are expressed as mean viral titers ±standard error of the mean. Statistical comparisons were made using the two-tailed Mann-Whitney test for non-parametric data. TFO-1 (SEQ ID 1) by itself had no measurable antiviral effect while TFO-3 (SEQ ID 3) alone reduced viral titers by 45%. TFO-1 (SEQ ID 1) and TFO-3 (SEQ ID 2) together had a synergistic antiviral effect giving a 10-fold decrease in viral titers over matching controls.

Example 10

Penetration of Red Light into the Human Trigeminal Ganglion (TG)

A preserved human cadaver was utilized to demonstrate that red light from a 150 mW laser source (wavelength 680 nm) can be directed from the Eustachian tube into the trigeminal ganglion (TG). A subsequent experiment on a fresh, unpreserved human specimen with the brain and dura removed was also performed. Light directed from an endoscope placed into the posterior nose penetrated into the human TG. A 150 Watt white light was directed from the endoscope through the nasal mucosa and bone and caused the human TG to glow bright red. These effects were visible to the naked eye and did not require any special detection techniques. No burning or other adverse effects were observed at the point of contact between the endoscope and nasal mucosa.

Example 11

Bioconjugation of Photofrin Monomers to TFO's

Photofrin®-TFO conjugates can be synthesized by a procedure that is analogous to the synthetic scheme developed for the synthesis of cobalamin-DNA bioconjugates. The hematoporphyrin polyether of commercially-available Photofrin® can be hydrolyzed in 0.1 M HCl at 4 degrees C. for 24 hrs to give the free hydroxyl derivative of hematoporphyrin. The hydroxyl-hematoporphyrin monomer is converted to the n-hydroxysuccinimidyl (NHS) ester and reacted with the oligonucleotide (TFO) that is still attached to the DNA synthesizer. Deprotection of the oligonucleotide bases shouldn't cleave the Photofrin®-DNA linkage, as shown by the previous synthesis of cobalamin-DNA bioconjugates. The Photofrin®-DNA conjugate is then purified by adsorption onto a Sep-Pak C-18 column (Waters, Inc.), followed by a wash with buffered water, elution with 20% acetonitrile in $H_2O$, and storage at −20 degrees.

Example 12

Photofrin Photodynamic Therapy

In the traditional PDT approach, Photofrin or a similar heme-based chromophore is attached via a stable linker to single-stranded TFO that specifically binds latent HSV-1. Intracellular Photofrin can be activated by red light (630-650 nm) in the presence of cellular oxygen to generate singlet oxygen. Subsequent radical reactions form superoxide and hydroxyl radicals that can degrade the herpes genome. This therapeutic approach is analogous to DNA-footprinting, in which hydroxyl radicals can degrade a proximal DNA strand. The dose of light delivered may be limited to produce oxygen radicals capable of cleaving the phosphodiester backbone of the herpes DNA but not capable of triggering an overtly cytotoxic response by oxidative overload (i.e. cellular necrosis or apoptosis).

Cy5-labeled TFO-3 (SEQ ID 2) was then synthesized and HPLC purified. 167 mcg of Cy5-TFO-3 (SEQ ID 2) was then systemically administered via an intraperitoneal injection into uninfected and latently infected Balb/c mice. The animals were sacrificed and dissected 6 or 24 hours after injection and the TG's imaged under a red laser light source (680 nm). An uninjected, uninfected mouse was also imaged as a control for autofluorescence (nil). Fluorescence of Cy5 was detectable in the TG's of Cy5-labeled TFO-3 (SEQ ID 2) treated mice.

Ex vivo delivery of TFOs was then performed by incubating latently infected mouse TG ex vivo for 1.5 hrs in a 42 micromolar solution of TFO-3. Intense red fluorescence was visible in TG neurons from this specimen, including neurons latently infected with HSV-1. This suggests that systemic administration of highly concentrated TFO-3 (SEQ ID 2) will result in uptake into TG neurons and their nuclei, the site of HSV-1 latency.

Example 13

Photodynamic Therapy

A red light absorbing molecule, such as cobalamin (vitamin $B_{12}$) can be attached to the DNA strand that is complementary to the herpes genome. The cobalamin molecules will attach to the TFO and prevent formation of a DNA triplex. The Co-C bond can then be cleaved by 590 nm yellow-orange light, releasing the TFO to bind the viral genome.

It has been demonstrated that bioconjugate derivatives of cobalamin tethered at the cobalt bond can be cleaved with a quantum yield of 0.25 at 590 nm. This is the long wavelength edge of the cobalamin absorption spectrum, but sufficient yellow-orange light penetrates the thin sinus tissue and bone underlying the human TG to allow for photocleavage of the Co—C bond, thereby releasing the cobalamin molecules from the oligonucleotide, and thereby allowing DNA triplex formation to occur. In this therapeutic approach, the photocleavable cobalamin moieties will block association of the complementary DNA to the herpes virus. Light-triggered cleavage of the Co—C bond will release cobalamin and allow for DNA triplex formation.

TFO sequences will be prepared on a DNA synthesizer according to established protocols. Two phosphorothioate linkages will replace the terminal phosphomonoester and phosphodiester residues at the 3'-end to increase stability against exonucleases. At the 5'-end, an extra residue with a 5'-primary amino linker will be incorporated. While the oligonucleotide is still attached to the solid support on the DNA synthesizer, the N-hydroxysuccinimidyl (NHS) ester of cobalamin will be introduced into the DNA synthesizer. The cobalamin NHS ester will react with the primary amine at the 5'-end of the synthesized oligonucleotide to create a covalent linkage between cobalamin and the synthesized DNA. Deprotection of the oligonucleotide bases will not cleave the cobalamin-DNA linkage, as shown by the previous synthesis of cobalamin-DNA bioconjugates. Because the synthesizer adds bases in the 3' to 5' direction, the modifier was the last step in synthesis of the cobalamin-DNA conjugate. The cobalamin-DNA conjugate will be purified by adsorption onto a Sep-Pak C-18 column (Waters, Inc.), followed by a wash with buffered water, elution with 20% acetonitrile in $H_2O$, and storage at −20 degrees. The NHS-ester of cobalamin has been synthesized previously and shown to be stable for months at 20 degrees C.

The cobalamin-DNA bioconjugate can be separated by visible light, thereby releasing the active drug only in the irradiated tissue. Human tissue is partially translucent to light in the range of 600-750 nm. Very little of this light is absorbed, so that no heat is felt if only red light is used to illuminate the skin and the intensity is diminished only by scattering. Intense light within this narrow wavelength range can be obtained from powerful diode lasers that have FDA-approval for therapeutic applications. Therefore, release of the drug with red light is easy to achieve with existing technology.

Example 14

TFO Conjugation with Pheophorbide

Many different types of photoactivateable agents may be attached to the TFOs of the present invention. In this Example, pheophorbide was conjugated to TFO-1 (SEQ ID 1) and TFO-3 (SEQ ID 2).

Ten μmoles of purified, reagent grade pheophorbide A (Frontier Scientific, Inc) was dissolved in 500 μl of dimethylformamide (DMF) and incubated with 11 μmoles of 1-(3-dimethylaminopropyl)-3-ethylcarbodiimide (EDCI) and 11 μmoles of N-hydroxysuccinimide (NHS) at 23 degrees C. in the dark for 6 hours. Samples of the reaction mixture were monitored by HPLC, showing the consumption of pheophorbide A and confirming the appearance of the NHS ester, the activated form of pheophorbide required for bioconjugation. Bioconjugation of the activated pheophorbide A NHS-ester to DNA was achieved by incubation for 1 hour at 23 degrees C. in the dark. The synthesis of the pheophorbide A-TFO-1 (SEQ ID 1) and pheophorbide-TFO-3 (SEQ ID 2) bioconjugates were confirmed by HPLC and mass spectroscopy.

Example 15

Anti-Viral Effect of TFOs Conjugated with Pheophorbide

Anti-herpes TFO-1 (SEQ ID 1) and TFO-3 (SEQ ID 2) were conjugated to pheophorbide as described in Example 14. The conjugates TFO-1-pheophorphorbide and TFO-3-pheophorbide were combined for this proof-of-principle experiment to give a final (total conjugate) concentration of 1, 10, and 100 nM. These were compared directly with free, unconjugated pheophorbide groups also at 1, 10, and 100 nM concentrations. These 6 groups (N=5 per group) were then exposed to 30 minutes of red light photoactivation. Controls included no light exposure and 30 minutes red light only (no pheophorbide in either control group). 4000 PFU/ml of HSV-1 was added to each group just before 30 minutes of red light photoactivation using a red light delivery apparatus. The read out was plaque-reduction as a measure of viral killing (final PFU/ml after treatment). The experiment was carried out in the dark. TFO-1 and-3-pheophorbide viral killing was compared with equivalent concentrations of free pheophorbide. Significance testing was performed using the 2-tailed Student's T-Test on the raw data where standard deviations of the groups were similar or the log-transformed data where standard deviations of the groups were significantly different, requiring log 10-transformation of the data to apply the t-test. There was significant viral plaque-inhibition at 10 nM (21% kill) with more plaque-inhibition at 100 nM (75% kill, $p<0.0001$) suggesting a dose-response.

There was a small antiviral effect (about 25% killing) of red light exposure compared with no exposure. This may be due to some heating from the red light source used for this experiment. There was a small (10%) protective effect of the anti-HSV DNA-pheophorbide conjugate at the lowest concentration (1 nM) compared with a similar concentration of free pheophorbide. This may be due to experimental error or, perhaps, a shielding effect of the DNA present in the solution. There was a small antiviral effect of 10 nM anti-HSV DNA-pheophorbide conjugate (about 20% killing) compared with a similar concentration of free pheophorbide. At the highest concentration tested (100 nM), the anti-HSV DNA-pheophorbide conjugate (TFO1,3-pheophorbide) killed 75% of the virus compared to a similar concentration of free pheophorbide.

All of the COMPOSITIONS and METHODS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

We claim:

1. A method for interfering with transcription at a target site in a herpes simplex type I (HSV-1) virus in a host cell comprising:
   (a) producing a triplex-forming oligonucleotide comprising SEQ ID NO:2;
   (b) coupling said oligonucleotide to a compound capable of introducing transcription-altering mutations in the HSV-1 viral genome; and
   (c) introducing said coupled oligonucleotide to said host cell under conditions appropriate for triplex formation.

2. The method of claim 1, wherein said compound is an activatable compound.

3. The method of claim 2, wherein said activatable compound is selected from the group consisting of psoralen, hematoporphyrin IX, chlorines, bacteriochlorins, phthalocyanines, hypocrellins, vitamin B12, a DNA crosslinker, an agent that induces DNA strand breaks, an agent that produces a reactive oxygen species, porphyrins, pheophorbide, pyropheophorbide, chlorine and bacteriochlorin.

* * * * *

SEQUENCE LISTING

<160> NUMBER OF SEQ ID NOS: 12

<210> SEQ ID NO 1
<211> LENGTH: 21
<212> TYPE: DNA
<213> ORGANISM: Artificial
<220> FEATURE:
<223> OTHER INFORMATION: binding sequence of the herpes LAT domain

<400> SEQUENCE: 1
gaagaggggg gggggaagaa g                                              21

<210> SEQ ID NO 2
<211> LENGTH: 24
<212> TYPE: DNA
<213> ORGANISM: Artificial
<220> FEATURE:
<223> OTHER INFORMATION: binding sequence of the herpes LAT domain

<400> SEQUENCE: 2
gggaggaggg agggaaggag gggg                                           24

<210> SEQ ID NO 3

```
<211> LENGTH: 18
<212> TYPE: DNA
<213> ORGANISM: Variola virus

<400> SEQUENCE: 3
agaagaagaa aagagaaa                                                  18

<210> SEQ ID NO 4
<211> LENGTH: 16
<212> TYPE: DNA
<213> ORGANISM: Variola virus

<400> SEQUENCE: 4
aaagaaaagg aggaag                                                    16

<210> SEQ ID NO 5
<211> LENGTH: 15
<212> TYPE: DNA
<213> ORGANISM: Variola virus

<400> SEQUENCE: 5
aaaggagaag gaaaa                                                     15

<210> SEQ ID NO 6
<211> LENGTH: 18
<212> TYPE: DNA
<213> ORGANISM: Variola virus

<400> SEQUENCE: 6 tctcccccctt tcttttttt                                                18

<210> SEQ ID NO 7
<211> LENGTH: 21
<212> TYPE: DNA
<213> ORGANISM: Variola virus

<400> SEQUENCE: 7
tttttttttt tttttttttt t                                              21

<210> SEQ ID NO 8
<211> LENGTH: 19
<212> TYPE: DNA
<213> ORGANISM: Variola virus

<400> SEQUENCE: 8
tccttctcct tcctcttct                                                 19

<210> SEQ ID NO 9
<211> LENGTH: 15
<212> TYPE: DNA
<213> ORGANISM: Variola virus

<400> SEQUENCE: 9
tctcttttct ctttc                                                     15

<210> SEQ ID NO 10
<211> LENGTH: 15
<212> TYPE: DNA
<213> ORGANISM: Variola virus

<400> SEQUENCE: 10
tctctctcct ctctt                                                     15
```

-continued

```
<210> SEQ ID NO 11
<211> LENGTH: 15
<212> TYPE: DNA
<213> ORGANISM: Variola virus

<400> SEQUENCE: 11
ttctcttctc ttttt                                                    15

<210> SEQ ID NO 12
<211> LENGTH: 16
<212> TYPE: DNA
<213> ORGANISM: Variola virus

<400> SEQUENCE: 12
ttctctttct ctcttc                                                   16
```